(12) United States Patent
Bai et al.

(10) Patent No.: US 8,889,619 B2
(45) Date of Patent: Nov. 18, 2014

(54) FUSION PROTEIN OF EXENDIN-4 AND ITS ANALOG, PREPARATION METHOD AND USE THEREOF

(75) Inventors: Xianhong Bai, Beijing (CN); Hua Tu, Beijing (CN); Xianzhong Li, Beijing (CN)

(73) Assignee: Beijing Dongfang Biotech Co., Ltd., Beijing (CN)

( * ) Notice: Subject to any disclaimer, the term of this patent is extended or adjusted under 35 U.S.C. 154(b) by 0 days.

(21) Appl. No.: 13/635,236

(22) PCT Filed: Jun. 10, 2011

(86) PCT No.: PCT/CN2011/075604
§ 371 (c)(1),
(2), (4) Date: Sep. 14, 2012

(87) PCT Pub. No.: WO2011/153965
PCT Pub. Date: Dec. 15, 2011

(65) Prior Publication Data
US 2013/0142795 A1    Jun. 6, 2013

(30) Foreign Application Priority Data

Jun. 11, 2010    (CN) .......................... 2010 1 0205166

(51) Int. Cl.
```
A61K 38/26      (2006.01)
A61P 3/10       (2006.01)
A61K 39/44      (2006.01)
C07K 14/575     (2006.01)
C07K 14/46      (2006.01)
C07K 16/00      (2006.01)
A61K 38/00      (2006.01)
```

(52) U.S. Cl.
CPC ......... C07K 14/575 (2013.01); C07K 14/57563 (2013.01); C07K 14/46 (2013.01); C07K 2319/30 (2013.01); C07K 16/00 (2013.01); *A61K 38/00* (2013.01)

USPC .......................... 514/7.2; 514/6.9; 424/134.1

(58) Field of Classification Search
None
See application file for complete search history.

(56) References Cited

U.S. PATENT DOCUMENTS

| | | | |
|---|---|---|---|
| 7,271,149 B2 * | 9/2007 | Glaesner et al. | ............... 514/7.2 |
| 7,544,657 B2 | 6/2009 | Ebbehoj et al. | |
| 2003/0082749 A1 | 5/2003 | Sun et al. | |
| 2004/0053370 A1 * | 3/2004 | Glaesner et al. | ............. 435/69.7 |
| 2006/0194719 A1 | 8/2006 | Ebbehoj et al. | |

FOREIGN PATENT DOCUMENTS

| | | |
|---|---|---|
| CN | 1403483 | 3/2003 |
| CN | 1483041 | 3/2004 |
| CN | 1935846 | 3/2007 |
| CN | 101273134 | 9/2008 |
| CN | 101891823 | 11/2010 |
| WO | 0246227 | 6/2002 |
| WO | 2007012188 | 2/2007 |

OTHER PUBLICATIONS

Bowie et al., 1990, Science 247: 1306-1310.*
Wells, 1990, Biochemistry 29:8509-8517.*
Kim et al., "Induction of insulin receptor substrate-2 expression by Fc fusion to exendin-4 overexpressed in E coli: a potential long acting glucagon-like peptide-1 mimetic," RMB reports (2009) 149(2):146-149.
Ming et al., "Cloning and prokaryotic expression of human lysozyme N-terminal fragment/Exendin-4 Chimeric peptide," Journal of Jinan University (Medicine Edition) (2009) 30(6):595-600.

* cited by examiner

*Primary Examiner* — Gyan Chandra
(74) *Attorney, Agent, or Firm* — Volpe and Koenig, P.C.

(57) ABSTRACT

Provided are a fusion protein of Exendin-4 and its analog, the preparation method and use thereof. The fusion protein is obtained by fusing of Exendin-4 or its analog to Fc region of human IgG2 via a linking peptide, which has the better stability and prolonged serum half-life, and can be used for treating diabetes and obesity.

9 Claims, 7 Drawing Sheets

SEQUENCE LISTING

```
<160> NUMBER OF SEQ ID NOS: 23

<210> SEQ ID NO 1
<211> LENGTH: 39
<212> TYPE: PRT
<213> ORGANISM: Artificial
<220> FEATURE:
<223> OTHER INFORMATION: The sequence is synthesized

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 2
<211> LENGTH: 30
<212> TYPE: PRT
<213> ORGANISM: Artificial
<220> FEATURE:
<223> OTHER INFORMATION: The sequence is synthesized

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 9
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (5)..(5)
<223> OTHER INFORMATION: Xaa=Gly, Ser, Ala, or Thr

<400> SEQUENCE: 3

Gly Gly Gly Gly Xaa Gly Gly Gly Gly
1               5

<210> SEQ ID NO 4
<211> LENGTH: 271
<212> TYPE: PRT
<213> ORGANISM: Artificial
<220> FEATURE:
<223> OTHER INFORMATION: The sequence is synthesized
<220> FEATURE:
```

```
<221> NAME/KEY: MISC_FEATURE
<222> LOCATION: (1)..(39)
<223> OTHER INFORMATION: the peptide hormone is the 1-39 amino acid,
      i.e. Exendin-4, and possesses the sequence shown by SEQ ID NO: 1
<220> FEATURE:
<221> NAME/KEY: MISC_FEATURE
<222> LOCATION: (40)..(48)
<223> OTHER INFORMATION: the linker is the 40-48 amino acid and has the
      sequence shown by SEQ ID NO: 3 (wherein Xaa is Ala)
<220> FEATURE:
<221> NAME/KEY: MISC_FEATURE
<222> LOCATION: (49)..(271)
<223> OTHER INFORMATION: the transport protein is the 49-271 amino acid,
      i.e. Fc fragment of IgG2

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser Gly Gly Gly Ala Gly Gly Gly
        35                  40                  45

Val Glu Cys Pro Pro Cys Pro Ala Pro Pro Val Ala Gly Pro Ser Val
50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser His Glu Asp Pro Glu
                85                  90                  95

Val Gln Phe Asn Trp Tyr Val Asp Gly Val Glu Val His Asn Ala Lys
            100                 105                 110

Thr Lys Pro Arg Glu Glu Gln Phe Asn Ser Thr Phe Arg Val Val Ser
        115                 120                 125

Val Leu Thr Val Val His Gln Asp Trp Leu Asn Gly Lys Glu Tyr Lys
130                 135                 140

Cys Lys Val Ser Asn Lys Gly Leu Pro Ala Pro Ile Glu Lys Thr Ile
145                 150                 155                 160

Ser Lys Thr Lys Gly Gln Pro Arg Glu Pro Gln Val Tyr Thr Leu Pro
                165                 170                 175

Pro Ser Arg Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Met Leu Asp Ser
210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255

His Asn His Tyr Thr Gln Lys Ser Leu Ser Leu Ser Pro Gly Lys
            260                 265                 270

<210> SEQ ID NO 5
<211> LENGTH: 271
<212> TYPE: PRT
<213> ORGANISM: Artificial
<220> FEATURE:
<223> OTHER INFORMATION: The sequence is synthesized

<400> SEQUENCE: 5

His Thr Glu Gly Thr Phe Thr Ser Asp Ala Ser Lys Gln Met Glu Glu
```

```
              1               5                  10                 15
            Glu Ala Val Arg Leu Phe Ile Glu Trp Leu Lys Asp Gly Gly Pro Ser
                           20                  25                 30

Ser Gly Ala Pro Pro Ser Gly Gly Gly Ala Gly Gly Gly Gly
                           35                  40                 45

Val Glu Cys Pro Pro Cys Pro Ala Pro Pro Val Ala Gly Pro Ser Val
                50                          55                 60

Phe Leu Phe Pro Pro Lys Pro Lys Asp Thr Leu Met Ile Ser Arg Thr
             65                          70                  75                 80

Pro Glu Val Thr Cys Val Val Val Asp Val Ser His Glu Asp Pro Glu
                                85                  90                 95

Val Gln Phe Asn Trp Tyr Val Asp Gly Val Glu Val His Asn Ala Lys
                               100                 105                110

Thr Lys Pro Arg Glu Glu Gln Phe Asn Ser Thr Phe Arg Val Val Ser
                               115                 120                125

Val Leu Thr Val Val His Gln Asp Trp Leu Asn Gly Lys Glu Tyr Lys
                               130                 135                140

Cys Lys Val Ser Asn Lys Gly Leu Pro Ala Pro Ile Glu Lys Thr Ile
            145                 150                 155                160

Ser Lys Thr Lys Gly Gln Pro Arg Glu Pro Gln Val Tyr Thr Leu Pro
                               165                 170                175

Pro Ser Arg Glu Glu Met Thr Lys Asn Gln Val Ser Leu Thr Cys Leu
                               180                 185                190

Val Lys Gly Phe Tyr Pro Ser Asp Ile Ala Val Glu Trp Glu Ser Asn
                               195                 200                205

Gly Gln Pro Glu Asn Asn Tyr Lys Thr Thr Pro Pro Met Leu Asp Ser
                               210                 215                220

Asp Gly Ser Phe Phe Leu Tyr Ser Lys Leu Thr Val Asp Lys Ser Arg
            225                 230                 235                240

Trp Gln Gln Gly Asn Val Phe Ser Cys Ser Val Met His Glu Ala Leu
                               245                 250                255

His Asn His Tyr Thr Gln Lys Ser Leu Ser Leu Ser Pro Gly Lys
                               260                 265                270

<210> SEQ ID NO 6
<211> LENGTH: 39
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(39)
<223> OTHER INFORMATION: different from SEQ ID NO:1 in 2 amino acid
      sites

<400> SEQUENCE: 6

His Thr Glu Gly Thr Phe Thr Ser Asp Ala Ser Lys Gln Met Glu Glu
 1               5                  10                 15

Glu Ala Val Arg Leu Phe Ile Glu Trp Leu Lys Asp Gly Gly Pro Ser
                20                  25                 30

Ser Gly Ala Pro Pro Ser
        35

<210> SEQ ID NO 7
<211> LENGTH: 271
<212> TYPE: PRT
<213> ORGANISM: Artificial
```

<220> FEATURE:
<223> OTHER INFORMATION: The sequence is synthesized

<400> SEQUENCE: 7

His Thr Glu Gly Thr Phe Thr Ser Asp Ala Ser Leu Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Gly Gly Gly Ala Gly Gly Gly
        35                  40                  45

Val Glu Cys Pro Pro Cys Pro Ala Pro Val Ala Gly Pro Ser Val
    50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser His Glu Asp Pro Glu
            85                  90                  95

Val Gln Phe Asn Trp Tyr Val Asp Gly Val Glu Val His Asn Ala Lys
            100                 105                 110

Thr Lys Pro Arg Glu Glu Gln Phe Asn Ser Thr Phe Arg Val Val Ser
        115                 120                 125

Val Leu Thr Val Val His Gln Asp Trp Leu Asn Gly Lys Glu Tyr Lys
    130                 135                 140

Cys Lys Val Ser Asn Lys Gly Leu Pro Ala Pro Ile Glu Lys Thr Ile
145                 150                 155                 160

Ser Lys Thr Lys Gly Gln Pro Arg Glu Pro Gln Val Tyr Thr Leu Pro
            165                 170                 175

Pro Ser Arg Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Met Leu Asp Ser
    210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
            245                 250                 255

His Asn His Tyr Thr Gln Lys Ser Leu Ser Leu Ser Pro Gly Lys
        260                 265                 270

<210> SEQ ID NO 8
<211> LENGTH: 39
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(39)
<223> OTHER INFORMATION: different from SEQ ID NO:1 in 3 amino acid
      sites

<400> SEQUENCE: 8

His Thr Glu Gly Thr Phe Thr Ser Asp Ala Ser Leu Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 9
<211> LENGTH: 271
<212> TYPE: PRT
<213> ORGANISM: Artificial
<220> FEATURE:
<223> OTHER INFORMATION: The sequence is synthesized

<400> SEQUENCE: 9

His Ala Glu Gly Thr Phe Thr Ser Asp Ala Ser Leu Thr Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser Gly Gly Gly Ala Gly Gly Gly Gly
        35                  40                  45

Val Glu Cys Pro Pro Cys Pro Ala Pro Val Ala Gly Pro Ser Val
    50                  55                  60

Phe Leu Phe Pro Pro Lys Pro Lys Asp Thr Leu Met Ile Ser Arg Thr
65                  70                  75                  80

Pro Glu Val Thr Cys Val Val Asp Val Ser His Glu Asp Pro Glu
                85                  90                  95

Val Gln Phe Asn Trp Tyr Val Asp Gly Val Glu Val His Asn Ala Lys
            100                 105                 110

Thr Lys Pro Arg Glu Glu Gln Phe Asn Ser Thr Phe Arg Val Val Ser
        115                 120                 125

Val Leu Thr Val Val His Gln Asp Trp Leu Asn Gly Lys Glu Tyr Lys
130                 135                 140

Cys Lys Val Ser Asn Lys Gly Leu Pro Ala Pro Ile Glu Lys Thr Ile
145                 150                 155                 160

Ser Lys Thr Lys Gly Gln Pro Arg Glu Pro Gln Val Tyr Thr Leu Pro
                165                 170                 175

Pro Ser Arg Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Met Leu Asp Ser
    210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255

His Asn His Tyr Thr Gln Lys Ser Leu Ser Leu Ser Pro Gly Lys
            260                 265                 270

<210> SEQ ID NO 10
<211> LENGTH: 39
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(39)
<223> OTHER INFORMATION: different from SEQ ID NO:1 in 4 amino acid
      sites

<400> SEQUENCE: 10

His Ala Glu Gly Thr Phe Thr Ser Asp Ala Ser Leu Thr Met Glu Glu
1               5                   10                  15

```
Glu Ala Val Arg Leu Phe Ile Glu Trp Leu Lys Asp Gly Gly Pro Ser
            20                  25                  30

Ser Gly Ala Pro Pro Ser
        35
```

<210> SEQ ID NO 11
<211> LENGTH: 271
<212> TYPE: PRT
<213> ORGANISM: Artificial
<220> FEATURE:
<223> OTHER INFORMATION: The sequence is synthesized

<400> SEQUENCE: 11

```
His Ala Glu Gly Thr Phe Thr Ser Asp Ala Ser Leu Thr Tyr Glu Glu
1               5                   10                  15

Glu Ala Cys Arg Leu Phe Ile Glu Trp Leu Lys Asp Gly Gly Pro Ser
            20                  25                  30

Ser Gly Ala Pro Pro Ser Gly Gly Gly Ala Gly Gly Gly
        35                  40                  45

Val Glu Cys Pro Pro Cys Pro Ala Pro Pro Val Ala Gly Pro Ser Val
50                  55                  60

Phe Leu Phe Pro Pro Lys Pro Lys Asp Thr Leu Met Ile Ser Arg Thr
65                  70                  75                  80

Pro Glu Val Thr Cys Val Val Val Asp Val Ser His Glu Asp Pro Glu
                85                  90                  95

Val Gln Phe Asn Trp Tyr Val Asp Gly Val Glu Val His Asn Ala Lys
            100                 105                 110

Thr Lys Pro Arg Glu Glu Gln Phe Asn Ser Thr Phe Arg Val Val Ser
        115                 120                 125

Val Leu Thr Val Val His Gln Asp Trp Leu Asn Gly Lys Glu Tyr Lys
130                 135                 140

Cys Lys Val Ser Asn Lys Gly Leu Pro Ala Pro Ile Glu Lys Thr Ile
145                 150                 155                 160

Ser Lys Thr Lys Gly Gln Pro Arg Glu Pro Gln Val Tyr Thr Leu Pro
                165                 170                 175

Pro Ser Arg Glu Glu Met Thr Lys Asn Gln Val Ser Leu Thr Cys Leu
            180                 185                 190

Val Lys Gly Phe Tyr Pro Ser Asp Ile Ala Val Glu Trp Glu Ser Asn
        195                 200                 205

Gly Gln Pro Glu Asn Asn Tyr Lys Thr Thr Pro Pro Met Leu Asp Ser
210                 215                 220

Asp Gly Ser Phe Phe Leu Tyr Ser Lys Leu Thr Val Asp Lys Ser Arg
225                 230                 235                 240

Trp Gln Gln Gly Asn Val Phe Ser Cys Ser Val Met His Glu Ala Leu
                245                 250                 255

His Asn His Tyr Thr Gln Lys Ser Leu Ser Leu Ser Pro Gly Lys
            260                 265                 270
```

<210> SEQ ID NO 12
<211> LENGTH: 39
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(39)
<223> OTHER INFORMATION: different from SEQ ID NO:1 in 6 amino acid -continued sites

<400> SEQUENCE: 12

His Ala Glu Gly Thr Phe Thr Ser Asp Ala Ser Leu Thr Tyr Glu Glu
1               5                   10                  15

Glu Ala Cys Arg Leu Phe Ile Glu Trp Leu Lys Asp Gly Gly Pro Ser
            20                  25                  30

Ser Gly Ala Pro Pro Ser
        35

<210> SEQ ID NO 13
<211> LENGTH: 263
<212> TYPE: PRT
<213> ORGANISM: Artificial
<220> FEATURE:
<223> OTHER INFORMATION: The sequence is synthesized

<400> SEQUENCE: 13

Ala Ala Glu Gly Thr Phe Thr Gly Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly Gly Gly Ala Gly Gly Gly Val Glu Cys Pro Pro Cys Pro Ala
        35                  40                  45

Pro Pro Val Ala Gly Pro Ser Val Phe Leu Phe Pro Pro Lys Pro Lys
    50                  55                  60

Asp Thr Leu Met Ile Ser Arg Thr Pro Glu Val Thr Cys Val Val Val
65                  70                  75                  80

Asp Val Ser His Glu Asp Pro Glu Val Gln Phe Asn Trp Tyr Val Asp
                85                  90                  95

Gly Val Glu Val His Asn Ala Lys Thr Lys Pro Arg Glu Glu Gln Phe
            100                 105                 110

Asn Ser Thr Phe Arg Val Val Ser Val Leu Thr Val Val His Gln Asp
        115                 120                 125

Trp Leu Asn Gly Lys Glu Tyr Lys Cys Lys Val Ser Asn Lys Gly Leu
130                 135                 140

Pro Ala Pro Ile Glu Lys Thr Ile Ser Lys Thr Lys Gly Gln Pro Arg
145                 150                 155                 160

Glu Pro Gln Val Tyr Thr Leu Pro Pro Ser Arg Glu Glu Met Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Met Leu Asp Ser Asp Gly Ser Phe Phe Leu Tyr Ser
    210                 215                 220

Lys Leu Thr Val Asp Lys Ser Arg Trp Gln Gln Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Pro Gly Lys
            260

<210> SEQ ID NO 14
<211> LENGTH: 31
<212> TYPE: PRT
<213> ORGANISM: Artificial

```
<220> FEATURE:
<223> OTHER INFORMATION: The sequence is synthesized
<220> FEATURE:
<221> NAME/KEY: MISC_FEATURE
<222> LOCATION: (1)..(31)
<223> OTHER INFORMATION: the amino acid sequence of GLP-1A8G

<400> SEQUENCE: 14

Ala Ala Glu Gly Thr Phe Thr Gly Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 15
<211> LENGTH: 262
<212> TYPE: PRT
<213> ORGANISM: Artificial
<220> FEATURE:
<223> OTHER INFORMATION: The sequence is synthesized

<400> SEQUENCE: 15

His Thr Glu Gly Thr Phe Thr Ser Asp Ala Ser Ser Tyr Leu Glu Gly
1               5                   10                  15

Gln Ala Cys Lys Glu Phe Ile Ala Trp Leu Val Lys Gly Arg Gly Gly
            20                  25                  30

Gly Gly Ala Gly Gly Gly Gly Val Glu Cys Pro Pro Cys Pro Ala Pro
        35                  40                  45

Pro Val Ala Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Gln Phe Asn Trp Tyr Val Asp Gly
                85                  90                  95

Val Glu Val His Asn Ala Lys Thr Lys Pro Arg Glu Glu Gln Phe Asn
            100                 105                 110

Ser Thr Phe Arg Val Val Ser Val Leu Thr Val Val His Gln Asp Trp
        115                 120                 125

Leu Asn Gly Lys Glu Tyr Lys Cys Lys Val Ser Asn Lys Gly Leu Pro
    130                 135                 140

Ala Pro Ile Glu Lys Thr Ile Ser Lys Thr Lys Gly Gln Pro Arg Glu
145                 150                 155                 160

Pro Gln Val Tyr Thr Leu Pro Pro Ser Arg Glu Glu Met Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Met Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 16
<211> LENGTH: 30
```

```
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(30)
<223> OTHER INFORMATION: different from SEQ ID NO:2 in 3 amino acid
      sites

<400> SEQUENCE: 16
```

| His | Thr | Glu | Gly | Thr | Phe | Thr | Ser | Asp | Ala | Ser | Ser | Tyr | Leu | Glu | Gly |
|---|---|---|---|---|---|---|---|---|---|---|---|---|---|---|---|
| 1 | | | | 5 | | | | | 10 | | | | | 15 | |

| Gln | Ala | Cys | Lys | Glu | Phe | Ile | Ala | Trp | Leu | Val | Lys | Gly | Arg |
|---|---|---|---|---|---|---|---|---|---|---|---|---|---|
| | | 20 | | | | | 25 | | | | | 30 | |

```
<210> SEQ ID NO 17
<211> LENGTH: 262
<212> TYPE: PRT
<213> ORGANISM: Artificial
<220> FEATURE:
<223> OTHER INFORMATION: The sequence is synthesized

<400> SEQUENCE: 17
```

| His | Thr | Glu | Gly | Thr | Phe | Thr | Ser | Asp | Leu | Ser | Ser | Tyr | Leu | Glu | Gly |
|---|---|---|---|---|---|---|---|---|---|---|---|---|---|---|---|
| 1 | | | | 5 | | | | | 10 | | | | | 15 | |

| Gln | Ala | Ser | Lys | Glu | Phe | Ile | Ala | Trp | Leu | Val | Lys | Gly | Arg | Gly | Gly |
|---|---|---|---|---|---|---|---|---|---|---|---|---|---|---|---|
| | | 20 | | | | | 25 | | | | | 30 | | | |

| Gly | Gly | Ala | Gly | Gly | Gly | Val | Glu | Cys | Pro | Pro | Cys | Pro | Ala | Pro |
|---|---|---|---|---|---|---|---|---|---|---|---|---|---|---|
| | 35 | | | | | 40 | | | | | 45 | | | |

| Pro | Val | Ala | Gly | Pro | Ser | Val | Phe | Leu | Phe | Pro | Pro | Lys | Pro | Lys | Asp |
|---|---|---|---|---|---|---|---|---|---|---|---|---|---|---|---|
| | 50 | | | | | 55 | | | | | 60 | | | | |

| Thr | Leu | Met | Ile | Ser | Arg | Thr | Pro | Glu | Val | Thr | Cys | Val | Val | Val | Asp |
|---|---|---|---|---|---|---|---|---|---|---|---|---|---|---|---|
| 65 | | | | | 70 | | | | | 75 | | | | | 80 |

| Val | Ser | His | Glu | Asp | Pro | Glu | Val | Gln | Phe | Asn | Trp | Tyr | Val | Asp | Gly |
|---|---|---|---|---|---|---|---|---|---|---|---|---|---|---|---|
| | | | | 85 | | | | | 90 | | | | | 95 | |

| Val | Glu | Val | His | Asn | Ala | Lys | Thr | Lys | Pro | Arg | Glu | Glu | Gln | Phe | Asn |
|---|---|---|---|---|---|---|---|---|---|---|---|---|---|---|---|
| | | | 100 | | | | | 105 | | | | | 110 | | |

| Ser | Thr | Phe | Arg | Val | Val | Ser | Val | Leu | Thr | Val | Val | His | Gln | Asp | Trp |
|---|---|---|---|---|---|---|---|---|---|---|---|---|---|---|---|
| | | | 115 | | | | | 120 | | | | | 125 | | |

| Leu | Asn | Gly | Lys | Glu | Tyr | Lys | Cys | Lys | Val | Ser | Asn | Lys | Gly | Leu | Pro |
|---|---|---|---|---|---|---|---|---|---|---|---|---|---|---|---|
| | 130 | | | | | 135 | | | | | 140 | | | | |

| Ala | Pro | Ile | Glu | Lys | Thr | Ile | Ser | Lys | Thr | Lys | Gly | Gln | Pro | Arg | Glu |
|---|---|---|---|---|---|---|---|---|---|---|---|---|---|---|---|
| 145 | | | | | 150 | | | | | 155 | | | | | 160 |

| Pro | Gln | Val | Tyr | Thr | Leu | Pro | Pro | Ser | Arg | Glu | Glu | Met | Thr | Lys | Asn |
|---|---|---|---|---|---|---|---|---|---|---|---|---|---|---|---|
| | | | | 165 | | | | | 170 | | | | | 175 | |

| Gln | Val | Ser | Leu | Thr | Cys | Leu | Val | Lys | Gly | Phe | Tyr | Pro | Ser | Asp | Ile |
|---|---|---|---|---|---|---|---|---|---|---|---|---|---|---|---|
| | | | 180 | | | | | 185 | | | | | 190 | | |

| Ala | Val | Glu | Trp | Glu | Ser | Asn | Gly | Gln | Pro | Glu | Asn | Asn | Tyr | Lys | Thr |
|---|---|---|---|---|---|---|---|---|---|---|---|---|---|---|---|
| | | | 195 | | | | | 200 | | | | | 205 | | |

| Thr | Pro | Pro | Met | Leu | Asp | Ser | Asp | Gly | Ser | Phe | Phe | Leu | Tyr | Ser | Lys |
|---|---|---|---|---|---|---|---|---|---|---|---|---|---|---|---|
| | 210 | | | | | 215 | | | | | 220 | | | | |

| Leu | Thr | Val | Asp | Lys | Ser | Arg | Trp | Gln | Gln | Gly | Asn | Val | Phe | Ser | Cys |
|---|---|---|---|---|---|---|---|---|---|---|---|---|---|---|---|
| 225 | | | | | 230 | | | | | 235 | | | | | 240 |

| Ser | Val | Met | His | Glu | Ala | Leu | His | Asn | His | Tyr | Thr | Gln | Lys | Ser | Leu |
|---|---|---|---|---|---|---|---|---|---|---|---|---|---|---|---|
| | | | | 245 | | | | | 250 | | | | | 255 | |

| Ser | Leu | Ser | Pro | Gly | Lys |
|---|---|---|---|---|---|
| | | | 260 | | |

```
<210> SEQ ID NO 18
<211> LENGTH: 30
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(30)
<223> OTHER INFORMATION: different from SEQ ID NO:2 in 3 amino acid
      sites

<400> SEQUENCE: 18

His Thr Glu Gly Thr Phe Thr Ser Asp Leu Ser Ser Tyr Leu Glu Gly
1               5                   10                  15

Gln Ala Ser Lys Glu Phe Ile Ala Trp Leu Val Lys Gly Arg
            20                  25                  30

<210> SEQ ID NO 19
<211> LENGTH: 262
<212> TYPE: PRT
<213> ORGANISM: Artificial
<220> FEATURE:
<223> OTHER INFORMATION: The sequence is synthesized

<400> SEQUENCE: 19

His Ala Glu Gly Thr Phe Thr Ser Asp Leu Ser Ser Tyr Leu Glu Gly
1               5                   10                  15

Gln Ala Ile Lys Glu Phe Ile Ala Trp Leu Val Lys Gly Arg Gly Gly
            20                  25                  30

Gly Gly Ala Gly Gly Gly Val Glu Cys Pro Pro Cys Pro Ala Pro
        35                  40                  45

Pro Val Ala Gly Pro Ser Val Phe Leu Phe Pro Pro Lys Pro Lys Asp
50                  55                  60

Thr Leu Met Ile Ser Arg Thr Pro Glu Val Thr Cys Val Val Val Asp
65                  70                  75                  80

Val Ser His Glu Asp Pro Glu Val Gln Phe Asn Trp Tyr Val Asp Gly
                85                  90                  95

Val Glu Val His Asn Ala Lys Thr Lys Pro Arg Glu Glu Gln Phe Asn
            100                 105                 110

Ser Thr Phe Arg Val Val Ser Val Leu Thr Val His Gln Asp Trp
        115                 120                 125

Leu Asn Gly Lys Glu Tyr Lys Cys Lys Val Ser Asn Lys Gly Leu Pro
    130                 135                 140

Ala Pro Ile Glu Lys Thr Ile Ser Lys Thr Lys Gly Gln Pro Arg Glu
145                 150                 155                 160

Pro Gln Val Tyr Thr Leu Pro Pro Ser Arg Glu Glu Met Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Met Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255
```

```
Ser Leu Ser Pro Gly Lys
            260

<210> SEQ ID NO 20
<211> LENGTH: 30
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(30)
<223> OTHER INFORMATION: different from SEQ ID NO:2 in 2 amino acid
      sites

<400> SEQUENCE: 20

His Ala Glu Gly Thr Phe Thr Ser Asp Leu Ser Ser Tyr Leu Glu Gly
1               5                   10                  15

Gln Ala Ile Lys Glu Phe Ile Ala Trp Leu Val Lys Gly Arg
            20                  25                  30

<210> SEQ ID NO 21
<211> LENGTH: 262
<212> TYPE: PRT
<213> ORGANISM: Artificial
<220> FEATURE:
<223> OTHER INFORMATION: The sequence is synthesized

<400> SEQUENCE: 21

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly Gly Ala Gly Gly Gly Val Glu Cys Pro Pro Cys Pro Ala Pro
        35                  40                  45

Pro Val Ala Gly Pro Ser Val Phe Leu Phe Pro Pro Lys Pro Lys Asp
        50                  55                  60

Thr Leu Met Ile Ser Arg Thr Pro Glu Val Thr Cys Val Val Val Asp
65                  70                  75                  80

Val Ser His Glu Asp Pro Glu Val Gln Phe Asn Trp Tyr Val Asp Gly
                85                  90                  95

Val Glu Val His Asn Ala Lys Thr Lys Pro Arg Glu Glu Gln Phe Asn
            100                 105                 110

Ser Thr Phe Arg Val Val Ser Val Leu Thr Val Val His Gln Asp Trp
        115                 120                 125

Leu Asn Gly Lys Glu Tyr Lys Cys Lys Val Ser Asn Lys Gly Leu Pro
    130                 135                 140

Ala Pro Ile Glu Lys Thr Ile Ser Lys Thr Lys Gly Gln Pro Arg Glu
145                 150                 155                 160

Pro Gln Val Tyr Thr Leu Pro Pro Ser Arg Glu Glu Met Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Met Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240
```

```
Ser Val Met His Glu Ala Leu His Asn His Tyr Thr Gln Lys Ser Leu
                245                 250                 255

Ser Leu Ser Pro Gly Lys
            260

<210> SEQ ID NO 22
<211> LENGTH: 278
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (1)..(39)
<223> OTHER INFORMATION: the peptide hormone is the 1-39 amino acid,
      i.e. Exendin-4, and possesses the sequence shown by SEQ ID NO: 1
<220> FEATURE:
<221> NAME/KEY: MISC_FEATURE
<222> LOCATION: (40)..(48)
<223> OTHER INFORMATION: the linker is the 40-48 amino acid and has the
      sequence shown by SEQ ID NO: 3 (wherein Xaa is Ala)
<220> FEATURE:
<221> NAME/KEY: MISC_FEATURE
<222> LOCATION: (49)..(278)
<223> OTHER INFORMATION: the transport protein is the 49-271 amino acid,
      i.e. Fc fragment of IgG4, same as WO/2005/000892

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser Gly Gly Gly Ala Gly Gly Gly
        35                  40                  45

Ala Glu Ser Lys Tyr Gly Pro Pro Cys Pro Pro Cys Pro Ala Pro Pro
    50                  55                  60

Phe Leu Gly Gly Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser Gln Glu Asp Pro Glu Val Gln Phe Asn Trp Tyr Val Asp Gly
            100                 105                 110

Val Glu Val His Asn Ala Lys Thr Lys Pro Arg Glu Glu Gln Phe Asn
        115                 120                 125

Ser Thr Tyr Arg Val Val Ser Val Leu Thr Val Leu His Gln Asp Trp
    130                 135                 140

Leu Asn Gly Lys Glu Tyr Lys Cys Lys Val Ser Asn Lys Gly Leu Pro
145                 150                 155                 160

Ser Ser Ile Glu Lys Thr Ile Ser Lys Ala Lys Gly Gln Pro Arg Glu
                165                 170                 175

Pro Gln Val Tyr Thr Leu Pro Pro Ser Gln Glu Glu Met Thr Lys Asn
            180                 185                 190

Gln Val Ser Leu Thr Cys Leu Val Lys Gly Phe Tyr Pro Ser Asp Ile
        195                 200                 205

Ala Val Glu Trp Glu Ser Asn Gly Gln Pro Glu Asn Asn Tyr Lys Thr
    210                 215                 220

Thr Pro Pro Val Leu Asp Ser Asp Gly Ser Phe Phe Leu Tyr Ser Arg
225                 230                 235                 240

Leu Thr Val Asp Lys Ser Arg Trp Gln Glu Gly Asn Val Phe Ser Cys
                245                 250                 255
```

```
Ser Val Met His Glu Ala Leu His Asn His Tyr Thr Gln Lys Ser Leu
            260                 265                 270

Ser Leu Ser Leu Gly Lys
        275

<210> SEQ ID NO 23
<211> LENGTH: 39
<212> TYPE: PRT
<213> ORGANISM: Artificial
<220> FEATURE:
<223> OTHER INFORMATION: The sequence is synthesized
<220> FEATURE:
<221> NAME/KEY: MISC_FEATURE
<222> LOCATION: (2)..(2)
<223> OTHER INFORMATION: Xaa=Gly, Thr, Ala, Ser, Leu, Ile, or Lys
<220> FEATURE:
<221> NAME/KEY: MISC_FEATURE
<222> LOCATION: (10)..(10)
<223> OTHER INFORMATION: Xaa=Leu, Ala, Ser, Leu, Ile, Glu, or Lys
<220> FEATURE:
<221> NAME/KEY: MISC_FEATURE
<222> LOCATION: (12)..(12)
<223> OTHER INFORMATION: Xaa=Lys, Leu, Thr, Ser, Leu, Ile, or Cys
<220> FEATURE:
<221> NAME/KEY: MISC_FEATURE
<222> LOCATION: (13)..(13)
<223> OTHER INFORMATION: Xaa=Gln, Thr, Ala, Val, Leu, Ile, or Lys
<220> FEATURE:
<221> NAME/KEY: MISC_FEATURE
<222> LOCATION: (14)..(14)
<223> OTHER INFORMATION: Xaa=Met, Tyr, Thr, Ala, Ser, Ile, or Lys
<220> FEATURE:
<221> NAME/KEY: MISC_FEATURE
<222> LOCATION: (19)..(19)
<223> OTHER INFORMATION: Xaa=Val, Cys, Ala, Ser, Leu, Ile, or Lys
<220> FEATURE:
<221> NAME/KEY: MISC_FEATURE
<222> LOCATION: (20)..(20)
<223> OTHER INFORMATION: Xaa=Arg, Thr, Tyr, Ser, Leu, Ile, or Lys
<220> FEATURE:
<221> NAME/KEY: MISC_FEATURE
<222> LOCATION: (21)..(21)
<223> OTHER INFORMATION: Xaa=Leu, Thr, Ala, Asp, Glu, His, or Lys
<220> FEATURE:
<221> NAME/KEY: MISC_FEATURE
<222> LOCATION: (24)..(24)
<223> OTHER INFORMATION: Xaa=Glu, Leu, Thr, Ala, Ser, Lys, or Ile
<220> FEATURE:
<221> NAME/KEY: MISC_FEATURE
<222> LOCATION: (27)..(27)
<223> OTHER INFORMATION: Xaa=Lys, Ala, Ser, Leu, Thr, Ile, or Lys
<220> FEATURE:
<221> NAME/KEY: MISC_FEATURE
<222> LOCATION: (28)..(28)
<223> OTHER INFORMATION: Xaa=Asp, Thr, Ala, Ser, Leu, Ile, or Lys
<220> FEATURE:
<221> NAME/KEY: MISC_FEATURE
<222> LOCATION: (30)..(30)
<223> OTHER INFORMATION: Xaa=Gly, Thr, Ala, Ser, Leu, Ile, or Arg
<220> FEATURE:
<221> NAME/KEY: MISC_FEATURE
<222> LOCATION: (31)..(31)
<223> OTHER INFORMATION: Xaa=Pro, Val, Ser, Ala, Leu, Ile, or Lys
<220> FEATURE:
<221> NAME/KEY: MISC_FEATURE
<222> LOCATION: (32)..(32)
<223> OTHER INFORMATION: Xaa=Ser, Thr, Glu, Ser, Asp, Lys, or Ile
<220> FEATURE:
<221> NAME/KEY: MISC_FEATURE
<222> LOCATION: (33)..(33)
<223> OTHER INFORMATION: Xaa=Thr, Ser, Ala, Met, Leu, Ile, or Lys
<220> FEATURE:
<221> NAME/KEY: MISC_FEATURE
<222> LOCATION: (34)..(34)
<223> OTHER INFORMATION: Xaa=Gly, Thr, Met, Ser, Ile, Leu, or Lys
<220> FEATURE:
<221> NAME/KEY: MISC_FEATURE
```

```
<222> LOCATION: (35)..(35)
<223> OTHER INFORMATION: Xaa=Ala, Thr, Ala, Glu, Leu, Ile, or Phe
<220> FEATURE:
<221> NAME/KEY: MISC_FEATURE
<222> LOCATION: (36)..(36)
<223> OTHER INFORMATION: Xaa=Pro, Ala, Thr, Ser, Leu, Ile, or Cys
<220> FEATURE:
<221> NAME/KEY: MISC_FEATURE
<222> LOCATION: (37)..(37)
<223> OTHER INFORMATION: Xaa=Pro, Thr, Ser, Ala, His, Lys, or Ile
<220> FEATURE:
<221> NAME/KEY: MISC_FEATURE
<222> LOCATION: (38)..(38)
<223> OTHER INFORMATION: Xaa=Pro, Thr, Val, Ser, Leu, Lys, or Ile
<220> FEATURE:
<221> NAME/KEY: MISC_FEATURE
<222> LOCATION: (39)..(39)
<223> OTHER INFORMATION: Xaa=Ser, Tyr, Ala, Leu, Ser, Ile, or Lys

<400> SEQUENCE: 23

His Xaa Glu Gly Thr Phe Thr Ser Asp Xaa Ser Xaa Xaa Xaa Glu Glu
1               5                   10                  15

Glu Ala Xaa Xaa Xaa Phe Ile Xaa Trp Leu Xaa Xaa Gly Xaa Xaa Xaa
            20                  25                  30

Xaa Xaa Xaa Xaa Xaa Xaa Xaa
        35
```

FUSION PROTEIN OF EXENDIN-4 AND ITS ANALOG, PREPARATION METHOD AND USE THEREOF

This application is a 35 U.S.C. §371 national phase application of PCT/CN2011/075604, which was filed Jun. 10, 2011 and is incorporated herein by reference as if fully set forth.

FIELD OF THE INVENTION

The present invention relates to a fusion protein, preparation method and use thereof. Specifically, the present invention relates to a long-acting fusion protein of Exendin-4 and its analog, nucleotide sequence encoding the fusion protein, vectors, host cells and pharmaceutical compositions, preparation method and use thereof.

DESCRIPTION OF THE RELATED ART

Exendin-4 is a peptide hormone, which comprises 39 amino acids and is capable of stimulating insulin secretion. In 2005, an injectable exenatide, Byetta® (a synthetic Exenatide-4), which had been developed by pharmaceuticals Eli Lilly and Emily together, had been approved for the treatment of diabetes, however, due to its small molecular weight, exenatide-4 is prone to be cleared quickly by kidney and thus not able to stimulate GLP-1R persistently, therefore, an acceptable efficacy could only be achieved by two injections per day, which causes much inconvenience to clinical treatment. Accordingly, developing a long-acting Exendin-4 pharmaceuticals would help improving its efficacy on type 1 and type 2 diabetes. Pharmaceutical investigators are attempting to prolong the persistent efficacy of drugs acting in vivo as anti-diabetics by modification of their molecular structures.

Against the status that the half-life of GLP-1 or Exendin-4 in vivo is short, investigators have developed corresponding fusion proteins, such as GLP-1 albumin fusion protein described in WO/2002/46227 or WO/2005/000892 or GLP-1-IgG4 fusion protein (Kim et al, Diabetes. 2003; 52(3): 751-759), but their binding activity in vitro is relatively low and efficacy thereof is inferior to Exendin-4. An ideal invention is one that was able to significantly prolong the half-life of the drug in vivo, and to maintain the anti-diabetic efficacy of Exendin-4, as well as to improve sensitivity of body to insulin; therefore, people are encouraged to make more efforts on developing long-acting factors of Exendin-4 and its analog with stable in vivo efficacy.

SUMMARY OF THE INVENTION

The present invention aims at providing a long-acting fusion protein of Exendin-4 and its analog with stable efficacy in vivo, corresponding nucleotide sequences, vectors, host cells and pharmaceutical compositions, preparation method and use thereof.

The fusion protein of Exendin-4 and its analog in the present invention is obtained by fusing Exendin-4 and its analog to the Fc fragments of immunoglobulin IgG2 via linker. It is used for the treatment of diabetes and obesity, as well as any other diseases which could benefit from lowering plasma glucose level, inhibiting gastrointestinal motility and gastric emptying. Due to their short half-lives, Exendin-4 and its analog need to be injected daily to maintain the efficacy, thus have certain limitation in clinical practice. In order to promote the therapeutic efficacy of this drug, the applicant conducted further studies and developed the fusion protein of Exendin-4 and its analog in this invention. And this fusion protein has higher stability and longer half-life in vivo, therefore could facilitate the reproduction and restoration of islet β cells according to the in vivo level of glucose, increase the amount of islet β cells, and thus promote the secretion of insulin and accelerate the sensitivity of body to insulin, and therefore have a superior anti-diabetic effect and minimal hypoglycemic risk, furthermore, it could also reduce the body weight and may also exert hypolipemic and hypotensive effect, thus protecting the cardiovascular system, as well as enhancing rest and memory function by acting on central nervous system to protect the nervous system.

The present invention provides a fusion protein, which is obtained by fusing peptide hormone to transport protein via linker, wherein, the said peptide hormone is Exendin-4 or analogue of Exendin-4, and the said peptide hormone is capable of lowering the blood glucose; the said transport protein is the Fc fragment of the immunoglobulin IgG2; the said fusion protein is capable of lowering the blood glucose.

The fusion protein of Exendin-4 and its analog provided in this invention is obtained by fusing Exendin-4 and its analog to the Fc fragments of immunoglobulin IgG2 via linker.

Wherein, the said Exendin-4 has the amino acid sequence as shown by SEQ ID NO:1, the said analog of Exendin-4 has any one selected from the group consisting of the derivative sequence of the amino acid sequence as shown by SEQ ID NO:1, the amino acid sequence as shown by SEQ ID NO:2, the derivative sequence of the amino acid sequence as shown by SEQ ID NO:2, the amino acid sequence of GLP-1 which is antigenic to DPP-IV and the derivative sequence of the amino acid sequence of GLP-1 which is antigenic to DPP-IV.

As part of the fusion protein, Exendin-4 or its analog is any one selected from the group consisting of Exendin-4 [SEQ ID NO: 1], GLP-1 (7-36) NH$_2$ [SEQ ID NO: 2], GLP-1 which is antigenic to DPP-IV, and the derivatives and fragments thereof.

It should be noted that, in this invention, the Exendin-4 and its analog should be understood as including any derivative of Exendin-4, GLP-1 (7-36) NH$_2$, GLP-1 which is antigenic to DPP-IV or fragment thereof, and they have the similar biological effect (i.e. hypoglycemic effect) as their originals. The derivatives include, but are not limited to, regular amino acid replacement, direct substitution and chemical modification of amino acid and so on.

The said Exendin-4 and its analog could be Exendin-4 sequence shown by SEQ ID NO: 1 and its derivatives and fragment. Wherein, the said Exendin-4 derivatives usually are preferably the peptide with 6 or less differences from the sequence shown by SEQ ID NO: 1, more preferably the peptides with 5 or less differences from the sequence shown by SEQ ID NO: 1, and most preferably the peptides with 4, 3, 2 or 1 difference(s) from the sequence shown by SEQ ID NO: 1, i.e., preferably, there are 6 or less, more preferably 5 or less, even more preferably 4 or less, further more preferably 3 or less, even further more preferably 2 or less, most preferably 1 or less amino acid site difference(s) between the said derivative sequence of the amino acid sequence shown by SEQ ID NO: 1 and the amino acid sequence shown by SEQ ID NO: 1.

Wherein, the said derivative sequence of the amino acid sequence shown by SEQ ID NO: 1 is preferably the fragment of the amino acid sequence shown by SEQ ID NO: 1, more preferably the amino acid sequence of the polypeptide stretching from amino acid 1 to amino acid 20 at N terminal of the amino acid sequence shown by SEQ ID NO: 1.

The fragment of Exendin-4 is the polypeptides stretching from amino acid 1 to amino acid 20 reserved at N terminal of the amino acid sequence shown by SEQ ID NO: 1.

The said Exendin-4 and its analog are preferably Exendin-4 which has the amino acid sequence shown by SEQ ID NO: 1.

The said Exendin-4 and its analog could be GLP-1 (7-36) NH$_2$ sequence shown by SEQ ID NO: 2, fragment and derivative thereof.

The said GLP-1 which is antigenic to DPP-IV is GLP-1A8G.

That is to say, the said peptide hormone comprises the sequence shown by Formula I:

His-Xaa$^2$-Glu-Gly-Thr-Phe-Thr-Ser-Asp-Xaa$^{10}$-Ser-Xaa$^{12}$-Xaa$^{13}$-Xaa$^{14}$-Glu-Glu-Glu-Ala-Xaa$^{19}$-Xaa$^{20}$-Xaa$^{21}$-Phe-Ile-Xaa$^{24}$-Trp-Leu-Xaa$^{27}$-Xaa$^{28}$-Gly-Xaa$^{30}$-Xaa$^{31}$-Xaa$^{32}$-Xaa$^{33}$-Xaa$^{34}$-Xaa$^{35}$-Xaa$^{36}$-Xaa$^{37}$-Xaa$^{38}$-Xaa$^{39}$  Formula I Wherein:
Xaa$^2$ may be Gly, Thr, Ala, Ser, Leu, Ile or Lys;
Xaa$^{10}$ may be Leu, Ala, Ser, Leu, Ile, Glu or Lys;
Xaa$^{12}$ may be Lys, Leu, Thr, Ser, Leu, Ile or Cys;
Xaa$^{13}$ may be Gln, Thr, Ala, Val, Leu, Ile or Lys;
Xaa$^{14}$ may be Met, Tyr, Thr, Ala, Ser, Ile or Lys;
Xaa$^{19}$ may be Val, Cys, Ala, Ser, Leu, Ile or Lys;
Xaa$^{20}$ may be Arg, Thr, Tyr, Ser, Leu, Ile or Lys;
Xaa$^{21}$ may be Leu, Thr, Ala, Asp, Glu, His or Lys;
Xaa$^{24}$ may be Glu, Leu, Thr, Ala, Ser, Lys or Ile;
Xaa$^{27}$ may be Lys, Ala, Ser, Leu, Thr, Ile or Lys;
Xaa$^{28}$ may be Asp, Thr, Ala, Ser, Leu, Ile or Lys;
Xaa$^{30}$ may be Gly, Thr, Ala, Ser, Leu, Ile or Arg;
Xaa$^{31}$ may be Pro, Val, Ser, Ala, Leu, Ile or Lys;
Xaa$^{32}$ may be Ser, Thr, Glu, Ser, Asp, Lys or Ile;
Xaa$^{33}$ may be Thr, Ser, Ala, Met, Leu, Ile or Lys;
Xaa$^{34}$ may be Gly, Thr, Met, Ser, Ile, Leu or Lys;
Xaa$^{35}$ may be Ala, Thr, Ala, Glu, Leu, Ile or Phe;
Xaa$^{36}$ may be Pro, Ala, Thr, Ser, Leu, Ile or Cys;
Xaa$^{37}$ may be Pro, Thr, Ser, Ala, His, Lys or Ile;
Xaa$^{38}$ may be Pro, Thr, Val, Ser, Leu, Lys or Ile;
Xaa$^{39}$ may be Ser, Tyr, Ala, Leu, Ser, Ile or Lys.

Wherein, the said linker is the peptide which has the sequence shown by (Gly)$_m$-Xaa-(Gly)$_n$, in which, m is an integer between 3 and 8, n is an integer between 3 and 8, Xaa is any one selected from the group consisting of Gly, Ser, Ala and Thr. The sequence shown by Formula I is the sequence shown by SEQ ID NO:23.

Wherein, m is preferably integers between 4 and 6, n is preferably integers between 4 and 6.

Wherein, the said linker preferably has the amino acid sequence shown by SEQ ID NO: 3.

Wherein, most preferably, the said fusion protein has the amino acid sequence shown by SEQ ID NO: 4.

The Fc fragment of IgG2 as part of the fusion protein originates from human.

The said IgG comprises Fc fragment of IgG, or fragment or derivative of Fc.

This invention also provides the polynucleotide sequence encoding the above mentioned fusion protein.

This invention also provides the vector comprising polynucleotide sequence.

This invention also provides the host cell transfected by the vector as above described, and the host cell as described may be CHO cell or NS0 cell.

According to the host cell provided by this invention, wherein, the said host cell is generated by transfecting the recipient cell by the vector as described above.

According to the host cell provided by this invention, wherein, the said recipient cell is CHO cell.

According to the host cell provided by this invention, wherein, the said recipient cell is NS0 cell.

This invention also provides a preparation method of fusion protein of Exendin-4 and its analog, which comprising the steps of transcripting and translating the said polynucleotide, as well as purifying using Protein A method.

This invention also provides a preparation procedure of fusion protein as described above, wherein, the procedure comprises of the following steps:
(1) transcripting and translating the polynucleotide sequence as mentioned above, (2) purifying the translation products of the polynucleotide sequence as mentioned above using Protein A method. After the fusion protein in this invention is expressed in the host cell, several protein purification methods may be used and also are well-known in the art, while choosing of purification method depends on production procedure and specific protein produced. For example, protein A or protein G affinity matrix may be used for effective purification of fusion protein including Fc fragment, and low or high pH buffer could be used to elute fusion protein from affinity matrix.

Methods for the characterizing the Exendin-4 fusion protein in this invention include: SDS-PAGE, Western-blot, isoelectric focusing electrophoresis, gel permeation chromatography, matrix assisted laser desorption/ionization mass spectrometry (MALDI-TOF), liquid chromatography-mass spectrometry (LC-MS).

This invention also provides a pharmaceutical composition, which comprising fusion protein of Exendin-4 and its analog and pharmacologically acceptable excipient. Wherein, the pharmaceutical composition as described comprises of fusion protein as described above and pharmacologically acceptable excipient.

The term "pharmacologically acceptable" used in this file is defined as molecule and its composition causing no unwanted, allergic or other adverse events when they are appropriately administered to animal and human. The "excipient" used in this file should be compatible to the fusion protein in this invention, i.e., usually it will not significantly decrease the efficacy of drug composition when mixed with the fusion protein.

The fusion protein in this invention could be formulated with one or more excipients. The fusion protein in this invention could be formulated into solution formulation or the formulation of injectable lyophiled powder which could be reconstituted with appropriate diluent.

The active fusion protein in this invention could be mixed with medicinal buffer to adjust the pH so as to provide acceptable stability and pH suitable for parenteral medication; one or more medicinal antibiotic agent(s) could be added; one or more medicinal saline solution(s) could be added to adjust the ionic strength or tension; one or more excipient(s) could be added to further adjust the isotonicity, such as glycerin and so on.

As for the excipient of the formulation, the extender could be saccharides, such as lactose, glucose and sucrose; starch, such as corn starch and potato starch; cellulose and its derivatives, such as sodium carboxymethylcellulose, ethyl cellulose and methyl cellulose; tragacanth powder; malt; gelatin; talc; solid lubricant, such as stearic acid and magnesium stearate; calcium sulphate; vegetable oil, such as peanut oil, cottonseed oil, sesame oil, olive oil, corn oil; polyol, such as propylene glycol, glycerol, sorbitol alcohol, mannose alcohol and polyethylene glycol; alginic acid; emulsifier, such as Tween; wetting agent such as sodium lauryl sulfate; coloring agent; flavoring agent; stabilizers; antioxidant; preservative; pyrogen-free water; isotonic salt solution; phosphate buffer; etc.

The medicinal salt form of the fusion protein in this invention is covered by this invention. Acids commonly used for prepare acid addition salt are inorganic acids, such as hydrochloric acid, hydrobromic acid, hydrogen iodate, sulfuric acid, phosphoric acid, and organic acids, such as para-toluenesulfonic acid, oxalic acid, citric acid, succinic acid, acetic acid and so on.

Alkali addition salts include salts deriving from inorganic bases, such as ammonium, alkali or alkaline earth metal hydroxides. Alkalis used in the preparation of the salt solution in this invention also include sodium hydroxide, potassium hydroxide, ammonium hydroxide, potassium carbonate and so on.

This invention also provides the administration route of the said pharmaceutical composition, which could be administered as local administration, aerosol or injection; the said injection may administered through intraperitoneal injection, subcutaneous injection, intramuscular injection and intravenous injection.

Wherein, the said pharmaceutical composition is administered as local administration, aerosol or injection. The said injection is administered through intraperitoneal injection, subcutaneous injection, intramuscular injection and intravenous injection.

The effective hypoglycemic dose of this fusion protein relays on many factors, which include, but are not limited to, subject's gender, body weight and age, administrative route and bioavailability, This invention also provides use of the fusion protein as described in the production of drugs against diabetes and obesity, The fusion protein in this invention has biological activity. Biological activity is defined as the in vivo capability of this fusion protein to bind and activate the GLP-1 receptor and arouse responses. The responses include, but are not limited to, the secretion of insulin, the inhibition of pancreatic glucagon, suppressing appetite, reducing body weight, inducing a feeling of fullness, suppressing apoptosis of pancreatic β cell, inducing proliferation and regeneration of pancreatic β cell. Example 4 (1) provides the in vitro experiment on the capability of the fusion protein to interact with and activate human GLP-1 receptors and induce the islet cell to secrete insulin. Example 4 (2) provides the in vivo hypoglycemic activity data of Ob/ob obese mice with diabetes and insulin resistant mouse model.

The fusion protein of Exendin-4 and its analog in this invention shows a significant anti-diabetic efficacy: through promoting the reproduction and restoration of islet β cells, it increases the amount of islet β cells, stimulates secretion of insulin, increases the sensitivity of body to insulin, and thus effectively controls the blood glucose level of type 2 and even type 1 diabetic patients and achieves long term treatment effect. The fusion protein in this invention exerts its biological activity through acting on "GLP-1" receptor, and could be used for the treatment of diabetes and obesity.

DETAILED DESCRIPTION OF EXEMPLARY EMBODIMENTS

The embodiment mode of this invention is described in the following examples. However, it should be noted that, the embodiment is not limited to certain details of these examples, since the other variation is well known or obvious based on directly disclosed content and attached claims for the normal skilled in the art. Therefore, any technology developed according to the content above of this invention falls in the range of this invention. The reference cited here are incorporated herein by citation as its entirety.

The experimental methods described in the following examples are all common technologies unless otherwise specified; the reagents and biological described are all commercially available unless otherwise specified.

EXAMPLE 1

The Synthesis of Expression Gene and Vector Construction of Exendin-4 Fusion Protein DNA construction of Exendin-4 fusion protein is achieved through gene synthesis by ligase chain reaction, and its protein sequence comprises as following:

```
                                                       [SEQ ID NO: 4]
HGEGTFTSDLSKQMEEEAVRLFIEWLKNGGPSSGAPPPSGGGGAGGGGVECPPCPAPPVAG

PSVFLFPPKPKDTLMISRTPEVTCVVVDVSHEDPEVQFNWYVDGVEVHNAKTKPREEQFN

STFRVVSVLTVVHQDWLNGKEYKCKVSNKGLPAPIEKTISKTKGQPREPQVYTLPPSREEM

TKNQVSLTCLVKGFYPSDIAVEWESNGQPENNYKTTPPMLDSDGSFFLYSKLTVDKSRWQ

QGNVFSCSVMHEALHNHYTQKSLSLSPGK*
```

Wherein, in the amino acid sequence shown by SEQ ID NO: 4, peptide hormone is the 1-39 amino acid, i.e. Exendin-4, and possesses the sequence shown by SEQ ID NO: 1; the linker is the 40-48 amino acid and has the sequence shown by SEQ ID NO: 3 (wherein Xaa is Ala); the transport protein is the 49-271 amino acid, i.e. Fc fragment of IgG2.

Figure 1:
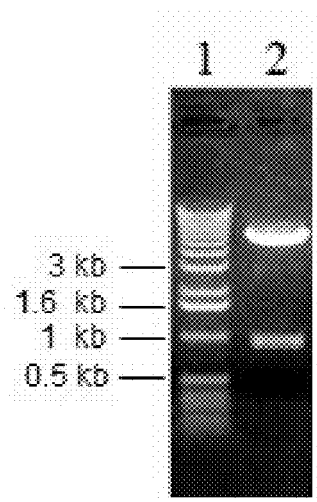
FIG. 1 shows the gel electrophoresis result of enzyme digested products of pHT112-SP-IgGH/Exendin-4/IgG2-Fc vector

First, the vector encoding Exendin-4 and human IgG2-Fc fusion protein for this fusion protein is constructed. IgG2-Fc domain comprises CH2 and CH3 part of IgG2 constant heavy chain. The leading peptide sequence SP-IgGH of IgG is fused with Exendin-4 so as to guide the fusion protein synthesized into the culture medium by means of secretion. The cDNA that encodes SP-IgGH/Exendin-4/IgG2 fusion protein (amino acid sequence for linker exists between Exendin-4 and IgG2) is synthesized by PCR and DNA automatic synthesizer and inserted between site Hind III and Not I of pHT112 vector (purchased from Yihu Biopharmaceutical Co., Ltd.) so as to construct pHT112-SP-IgGH/Exendin-4/IgG2-Fc vector. Exendin-4/IgG2-Fc with secretion ability comprises IgG2 constant heavy chain (CH2 and CH3). The SP-IgGH secretion leading peptide sequence fuses with Exendin-4 sequence so as to induce the secretion of the protein synthesized into cell nutrient solution. FIG. 1 shows the result of pHT112-SP-IgGH/Exendin-4/IgG2-Fc vector reflected in agarose gel electrophoresis after digested by a pair of endonucleases, Hind III and Not I. Endonucleases, Hind III and Not I, deletes 880 base pairs of DNA insert, including SP-IgGH/Exendin-4/IgG2-Fc.

EXAMPLE 2

The Construction, Expression and Purification of Engineering Cell Line for Exendin-4 Fusion Protein 1. The Construction of Engineering Cell Line for Exendin-4 Fusion Protein Chinese hamster ovary cell (CHO) is cultured in DMEM (purchased from Invitrogen) complete culture solution with 10% (volume percentage) fetal calf serum (FCS), and spread evenly onto 6 well plate one day before transfection with $3 \times 10^5$ cells per well. For the transfection, referring to LIPOFECTAMINE 2000 instruction. 48 h after transfection, the cells are compressingly cultured in selective substrate (methionine sulphoximine (MSX) 25 μM) for approximately one week, then empty cells are all dead, and the surviving cells are inoculated in 96 well plates (50 cells/well) for further compressing culture. After the cell is cloned, ELISA test is used to determine the protein expression amount in the culture supernatant, wells with high expression (expression amount excesses 200 mg/L) are screened and transferred to 24 well plates for amplification culture. ELISA is carried out again to determine the protein expression in supernatant, and according to reference (*Cell Experimental Manual*, Science Press, 2003), cell lines with high expression (expression amount excesses 200 mg/L) are screened and continue with amplification culture, and through gradual domesticated suspension culture, seed cell bank is established and sub cloning is carried out so as to establish working cell bank (composed of CHO engineering cell line).

2. Purification of Exendin-4 Fusion Protein

CHO engineering cell line obtained above is thawed and inoculated in a 25 cm² T flask, each with 5 ml, cell suspension, after shaking culture for 4-5 days, the content is amplified into triangular flask and further cultured for 7-10 days, according to the procedure in reference (*Molecular Cloning*, Science Press, 2002), the cell culture fluid with fusion protein is separated and purified sequentially by Protein A affinity chromatography media (MabSuRe™, GE company), anion chromatography media (Q Sepherose FF, GE company), cation chromatography media (SP Sepherose FF, GE company), then purified fusion protein is obtained through replacement into formulation buffer by G-25 gel filtration column.

EXAMPLE 3

Analysis on the Structure of Exendin-4 Fusion Protein

1. Western Blot Assay

Figure 2:
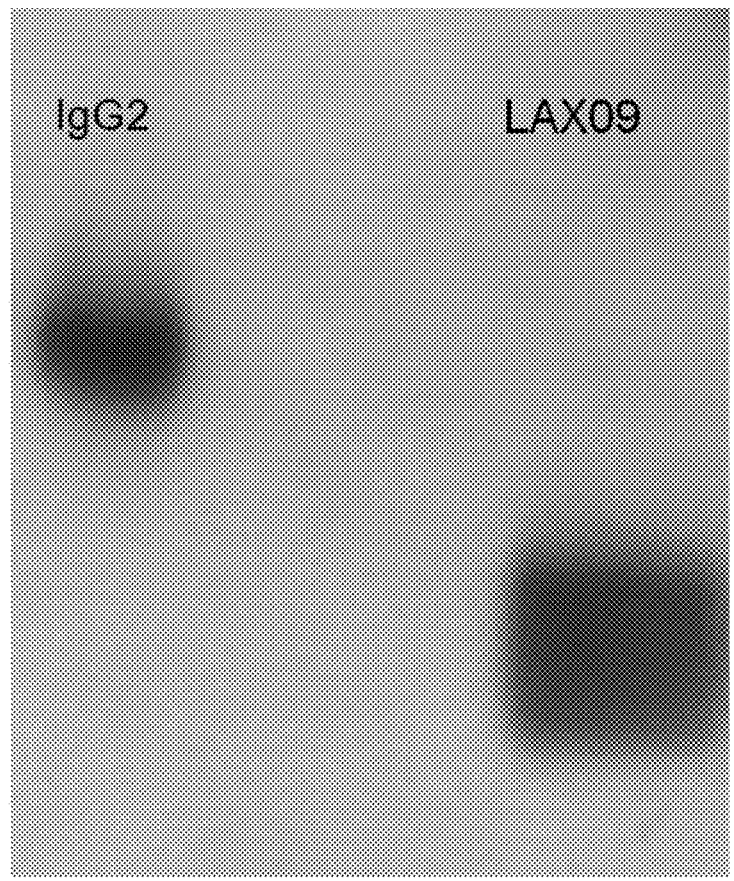
FIG. 2 shows the immunological identification atlas of Exendin-4 fusion protein

After the purified fusion protein is put through non-reductive electrophoresis, the electrophoretic band is transferred onto PVDF membrane activated by methanol through transfer device (GE company) (current: 25 mA, time: 2 h). The PVDF membrane is sealed in 5 wt % skimmed milk for 2 h, then incubates in pre-diluted anti IgG2 antibody labeled through addition of alkaline phosphatase for 1 h and is washed with TBST, which should be replaced with fresh one each 5 min during washing, after washing is completed, CDP-star luminescence assay substrate is added and the film is pressed for exposure and imaging. The result is shown in FIG. 2, fusion protein shows positive for IgG2 antibody.

2. Isoelectric Focusing Electrophoresis Assay

Figure 3:
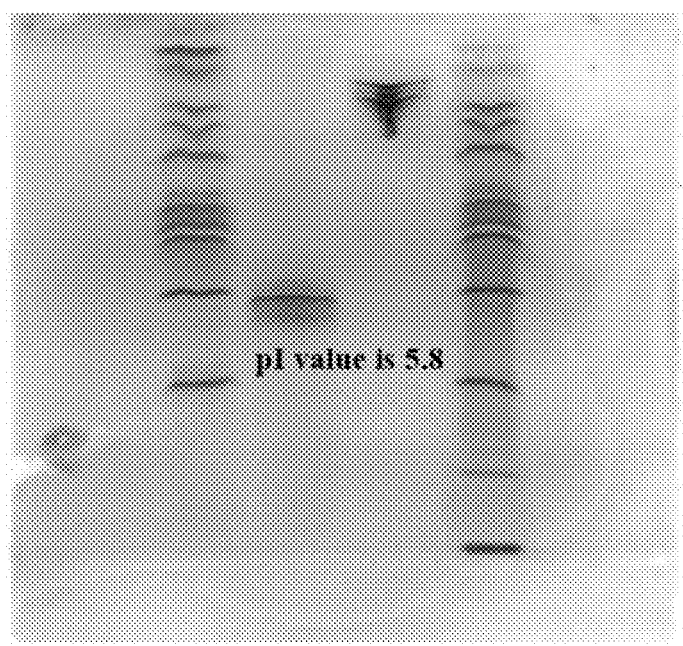
FIG. 3 shows the isoelectric focusing electrophoresis atlas of Exendin-4 fusion protein

The purified fusion protein is assayed through isoelectric focusing electrophoresis with rapid electrophoresis system (Phast System, GE), for which pre-prepared gel with pH 3-10 is used, and when the focusing electrophoresis is done, the pre-prepared gel is stained with Coomassie solution. The result is shown in FIG. 3. The isoelectric point in the main band of fusion protein is 5.8, which is close to the expected value of 6.2.

3. Gel Chromatography Assay Purification

Figure 4:
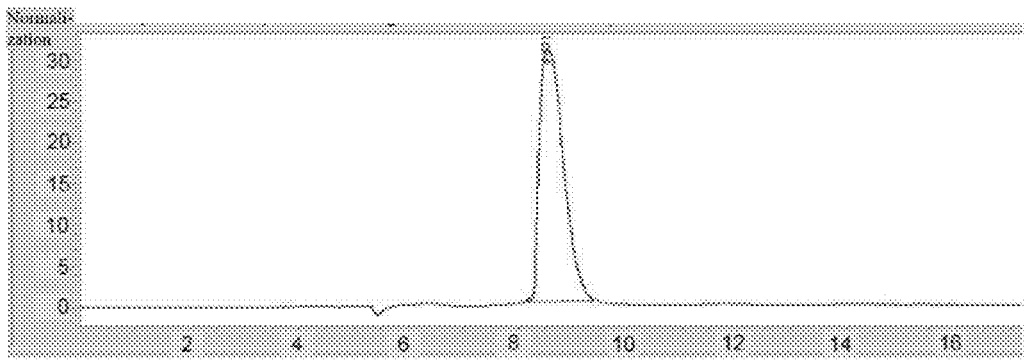
FIG. 4 shows the gel chromatography atlas of Exendin-4 fusion protein

The purified fusion protein is assayed by gel chromatography (chromatographic column TSK3000sw) according to the procedure in reference ((*Molecular Cloning*, Science Press, 2002)), with a loading amount of 10 μg. The result is shown in FIG. 4, the fusion protein shows as single, symmetrical peak in the gel chromatography, and the retention time is 8.5 min.

EXAMPLE 4

The Bioactivity of Exendin-4 Fusion Protein

1. In Vitro Activity of Exendin-4 Fusion Protein:
A. cAMP Secretion Test of Exendin-4 Fusion Protein on Human GLP-1 Receptor CHO Cell The cellular level test on the bioactivity of fusion protein is conducted with CHO-hGLP1R cell expressing GLP-1 receptor (as described in reference WO/2007/017892), to determine the molar concentration of downstream effect product (the second massager cAMP) and in vitro performance of this invention LAX09 (i.e. the Exendin-4 fusion protein obtained as described above and shown by SEQ ID NO: 4, the same below). DMEM substrate containing 10% volume FBS is added into 96 black transparent well plate, and Exendin-4 and LAX09 with drug concentration from 0.01 nM to 1000 nM are added into substrate respectively, after incubation for 30 minutes, the cell is disintegrated and the intracellular cAMP concentration is tested by commercial kit (Cisbio), the result is shown in Table 1.

TABLE 1

| Test on Ratio of cAMP Concentration in Cell Expressing Human GLP-1 Receptor | | | | | | | |
|---|---|---|---|---|---|---|---|
| Drug concentration (nM) | | 0.01 | 0.1 | 1 | 10 | 100 | 1000 |
| cAMP concentration | Exendin-4 | 2 | 5 | 48 | 135 | 155 | 140 |
|  | LAX09 | 2 | 5 | 31 | 115 | 155 | 153 |

Figure 5:
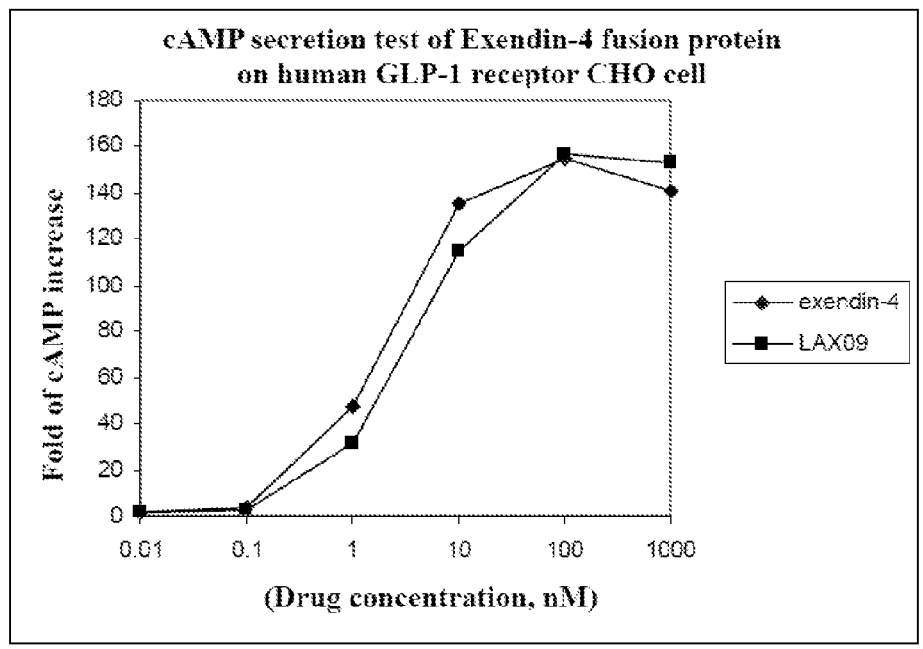
FIG. 5 shows the result of cAMP concentration variation in CHO-hGLP1R cells after being treated with Exendin-4 fusion protein

$EC_{50}$ of LAX90 is around 4.5 nM, and $EC_{50}$ of Exendin-4 is around 2.5 nM; the two are close. Therefore, LAX09 in this invention could produce a GLP-1 receptor activation level similar to Exendin-4. As shown in FIG. 5.

B. The Combining Test of LAX09 with CHO Engineering Cell Line Expressing Human GLP-1R A test on the combining activity of LAX09 with CHO engineering cell line (CHO-hGLP1R, the same below) which could persistently express human GLP-1 receptor is carried out to determine the bioactivity of purified sample of the invention LAX09.

CHO-hGLP1R cell line combining test: CHO engineering strain stably expressing human GLP-1R is made into single cell suspension, and the cell density is adjusted to 10,000,000 cells/mL through PBS, LAX09 sample is diluted into different concentration gradient, in each viral, 20 μL cell suspension is mixed with 20 μL samples with different concentration respectively, and they were incubated at 4° C. for 30 min. After PBS washing, human immunoglobulin γ chain antibody labeled with fluorescein FITC is added, and incubate at 4° C. for 30 min. After PBS washing, 1% paraformaldehyde in PBS is added, mix thoroughly and load the sample, read the mean fluorescence intensity of sample of each concentration in selected zone in the flow cytometry. As shown in Table 2.

TABLE 2

Test on Combining Activity of LAX09 with Cell Expressing Human GLP-1 Receptor

| | LAX09 mass Concentration (μg/mL) | | | | | | | |
|---|---|---|---|---|---|---|---|---|
| 0 | 0.098 | 0.246 | 0.614 | 1.536 | 3.84 | 9.6 | 24 | 60 |

| Mean fluorescence intensity | 10.19 | 14.12 | 17.53 | 21.78 | 38.01 | 57.03 | 81.54 | 94.81 | 121.98 |

2. In Vivo Activity of Exendin-4 Fusion Protein:

A. KK-Ay Mouse Obesity Diabetic Model

Figure 6:
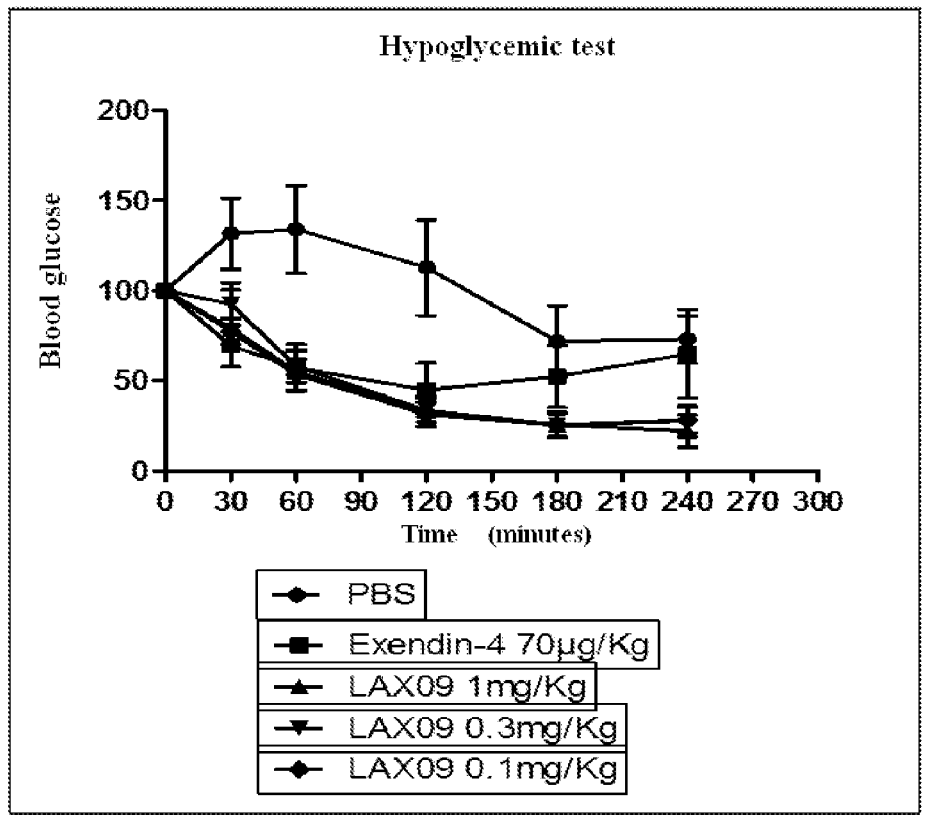
FIG. 6 shows the hypoglycemic effect of single Exendin-4 fusion protein injection in KK-Ay mouse obesity diabetic model

Single injection hypoglycemic test: KK-Ay diabetic model mice (purchased from Beijing, Beijing HFK Bioscience Co., Ltd, the same below) are randomized into 4 groups, including one PBS control group and three experimental groups of different Exendin-4 fusion protein (LAX 09) gradients. After fasting for 2 h, the animals are injected with the drug through caudal vein, with a volume of 200 μl/animal, then the blood glucose of the mice at 0 min, 30 min, 60 min, 120 min, 180 min and 240 min is determined, the result is shown in FIG. 6, LAX09 has the best hypoglycemic effect at 1 mg/Kg, with the blood glucose of the mouse being controlled under 10 mmol/L.

Figure 7:
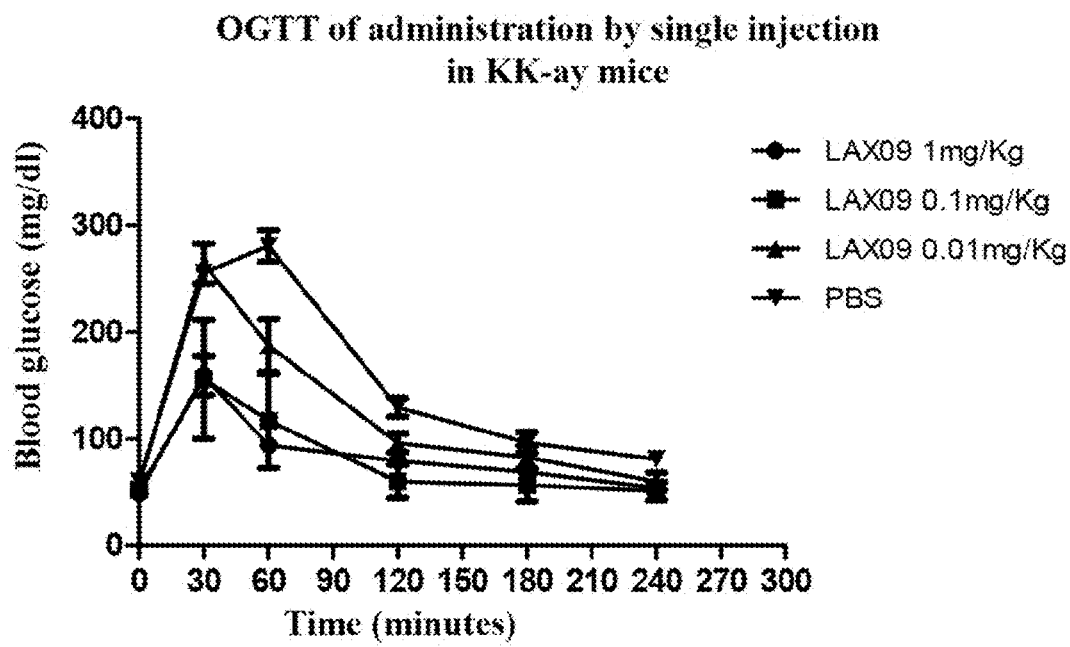
FIG. 7 shows the oral glucose tolerance result of Exendin-4 fusion protein in KK-Ay mouse obesity diabetic model

Oral glucose tolerance test: KK-Ay diabetic model mice are randomized into 4 groups, including one PBS control group and three experimental groups of different Exendin-4 fusion protein (LAX 09) gradients. After fasting for 16 h, the animals are injected with the drug subcutaneously with a volume of 200 μl/animal, 6 h later, glucose is given through gastric tube according to their body weight (1 mg/g), then the blood glucose of the mice at 0 min, 30 min, 60 min, 120 min, 180 min and 240 min is determined, the result is shown in FIG. 7, mice in 1 mg/Kg group and 0.1 mg/Kg group possess the same good ability to maintain normal blood glucose.

Figure 8:
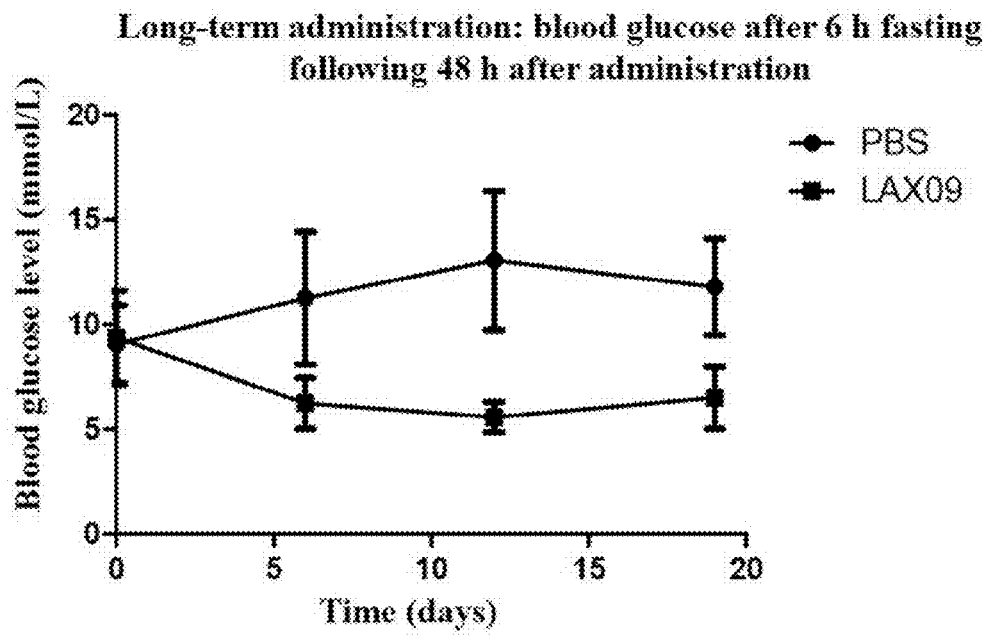
FIG. 8 shows the influence of long-term Exendin-4 fusion protein administration on the blood glucose in KK-Ay mouse obesity diabetic model
Figure 9:
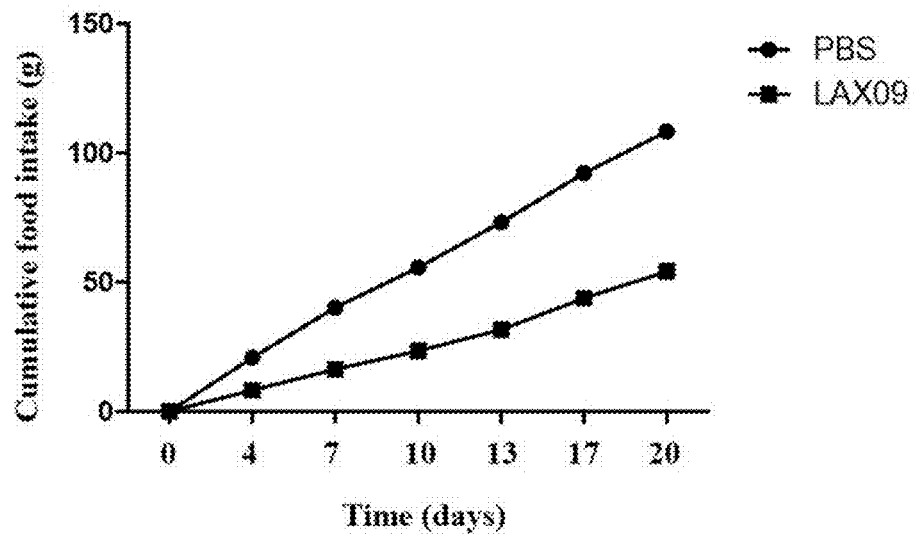
FIG. 9 shows the influence of long-term Exendin-4 fusion protein administration on the food intake of mouse
Figure 10:
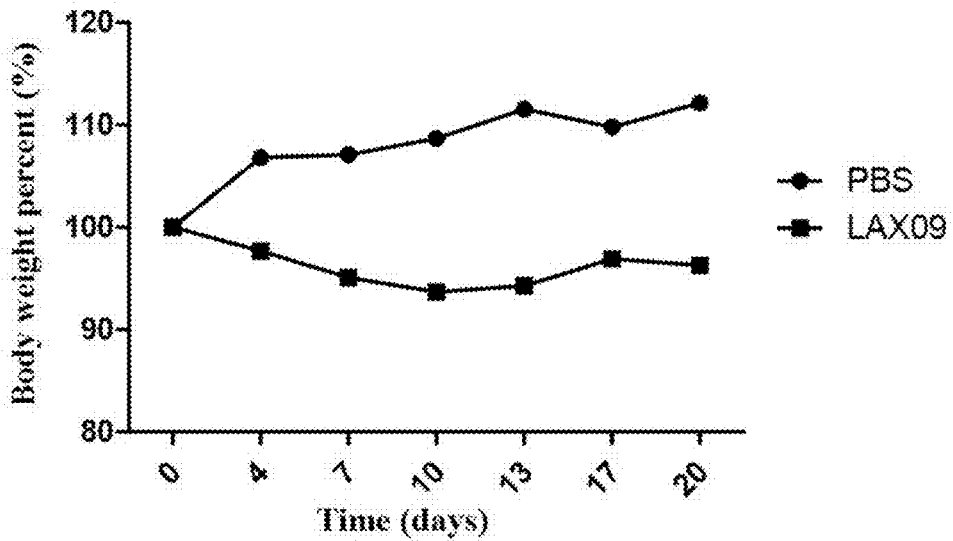
FIG. 10 shows the influence of long-term Exendin-4 fusion protein administration on the body weight of mouse
Figure 11:
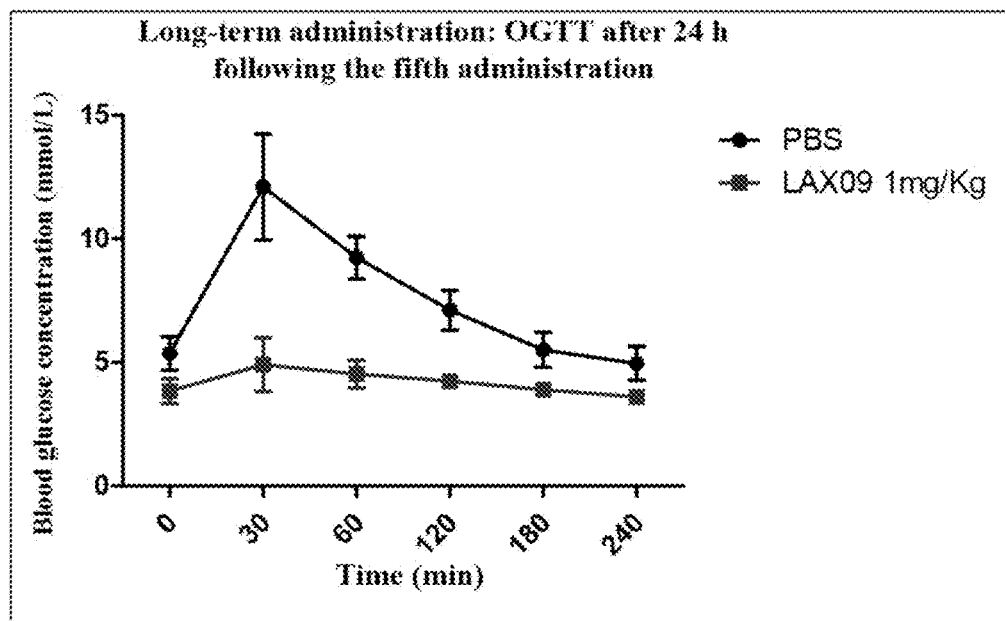
FIG. 11 shows the oral glucose tolerance result within 24 hours after administration of long-term Exendin-4 fusion protein treatment
Figure 12:
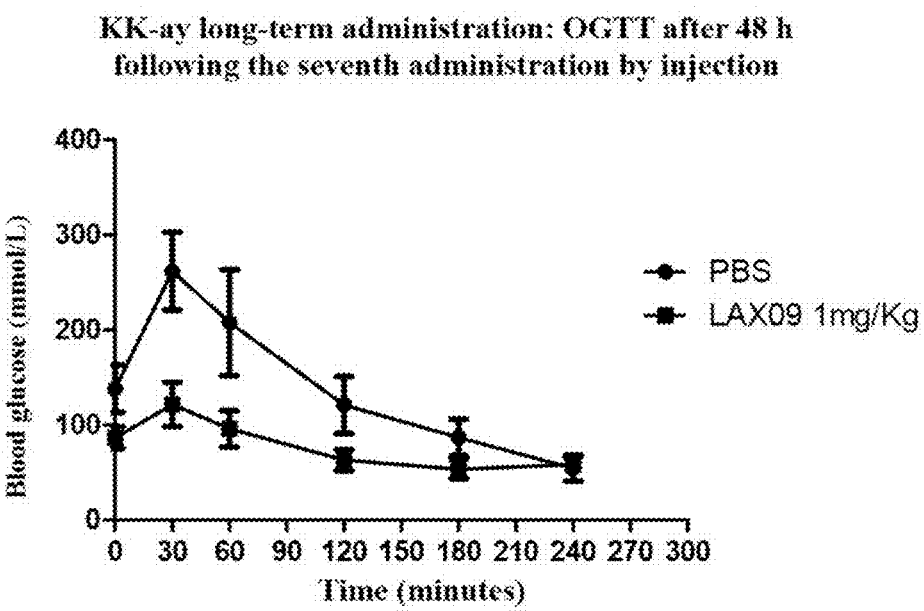
FIG. 12 shows the oral glucose tolerance result within 48 hours after administration of long-term Exendin-4 fusion protein treatment

Long-term administration experiment: KK-Ay diabetic model mice are randomized into 2 groups, including PBS group and 1 mg/Kg Exendin-4 fusion protein (LAX 09) experimental group. The drug is given twice per week, and the mice are fasted for 6 h each Wednesday and tested for fast blood glucose, meanwhile their food intake and weight variation are recorded. The result is shown in FIG. 8, the fast blood glucose of the mice in the experimental group is significantly different from that of PBS group; the food intake decreases, as shown in FIG. 9, the weight is significantly reduced, as shown in FIG. 10. 24 hours after the medication, the result of oral glucose tolerance test is as shown in FIG. 11. 48 hours after the medication, the result of oral glucose tolerance test is as shown in FIG. 12. All these results demonstrate significant efficacy of Exendin-4 fusion protein.

B. Db-Db Mouse Obesity Diabetic Model

Figure 13:
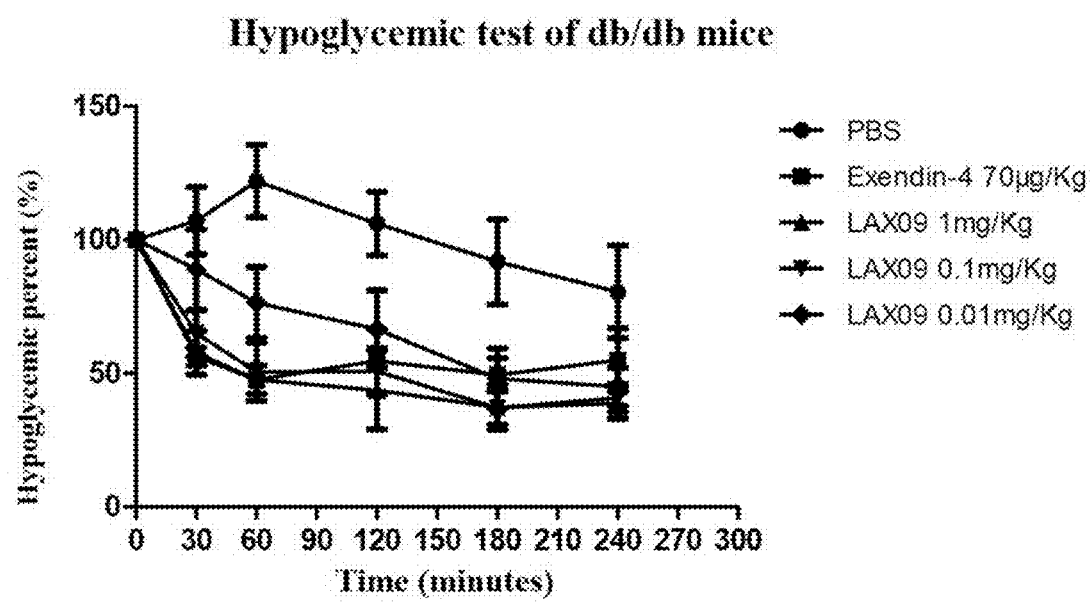
FIG. 13 shows the influence of Exendin-4 fusion protein on the blood glucose in db/db mouse obesity diabetic model

Single injection hypoglycemic test: db/db diabetic model mice aged at 5-6 weeks are randomized into 4 groups, including one PBS control group and three experimental groups of different Exendin-4 fusion protein (LAX 09) gradients. After fasting for 2 h, the animals are injected with the drug through caudal vein, with a volume of 200 μl/animal, then the blood glucose of the mice at 0 min, 30 min, 60 min, 120 min, 180 min and 240 min is determined, the result is shown in FIG. 13, 1 mg/Kg group and 0.1 mg/Kg group have the best hypoglycemic effect.

EXAMPLE 5

According to the sample procedure used in example 1-4, fusion protein in Table 3 is prepared and determined for in vivo and in vitro efficacy.

TABLE 3

Fusion Protein and Its Relative Bioactivity

| Fusion protein sequence | Peptide hormone sequence | Linker peptide sequence | Transport protein sequence | Relative bioactivity* (%) |
|---|---|---|---|---|
| SEQ ID NO: 5 | SEQ ID NO: 6 | SEQ ID NO: 3 | IgG2-Fc | 99 |
| SEQ ID NO: 7 | SEQ ID NO: 8 | SEQ ID NO: 3 | IgG2-Fc | 98 |
| SEQ ID NO: 9 | SEQ ID NO: 10 | SEQ ID NO: 3 | IgG2-Fc | 97 |
| SEQ ID NO: 11 | SEQ ID NO: 12 | SEQ ID NO: 3 | IgG2-Fc | 96 |
| SEQ ID NO: 13 | SEQ ID NO: 14 | SEQ ID NO: 3 | IgG2-Fc | 95 |
| SEQ ID NO: 15 | SEQ ID NO: 16 | SEQ ID NO: 3 | IgG2-Fc | 94 |
| SEQ ID NO: 17 | SEQ ID NO: 18 | SEQ ID NO: 3 | IgG2-Fc | 93 |
| SEQ ID NO: 19 | SEQ ID NO: 20 | SEQ ID NO: 3 | IgG2-Fc | 92 |
| SEQ ID NO: 21 | SEQ ID NO: 2 | SEQ ID NO: 3 | IgG2-Fc | 91 |
| SEQ ID NO: 22 | SEQ ID NO: 1 | SEQ ID NO: 3 | IgG4-Fc | 75 |

*Relative bioactivity is defined as the relative ratio between the fast blood glucose decrease (compared to blank control group) of the fusion protein determined through long administration experiment (KK-Ay diabetic model mouse) among KK-Ay mouse obese diabetic model and the corresponding value of purified fusion protein obtained in example 2.

Specifically, long term administration is conducted according to the following protocol: the KK-Ay diabetic model mice are randomized into blank control group (injected only with PBS) and experimental group (injected with 1 mg/Kg of the fusion protein in Table 3). The drug is given twice per week; after 2 weeks, the mice are fasted for 6 h and tested for fasting blood glucose, and the blood glucose decrease of one experimental group is calculated by subtracting the fasting blood glucose of the experimental group from that of the blank control group.

Wherein, SEQ ID NO:6 is different from SEQ ID NO:1 in 2 amino acid sites, and has the sequence of formula I; SEQ ID NO:8 is different from SEQ ID NO:1 in 3 amino acid sites, and has the sequence of formula I; SEQ ID NO:10 is different from SEQ ID NO:1 in 4 amino acid sites, and has the sequence of formula I; SEQ ID NO:12 is different from SEQ ID NO:1 in 6 amino acid sites, and has the sequence of formula I; SEQ ID NO:14 is the amino acid sequence of GLP-1A8G; SEQ ID NO:16 is different from SEQ ID NO:2 in 3 amino acid sites; SEQ ID NO:18 is different from SEQ ID NO:2 in 3 amino acid sites, SEQ ID NO:20 is different from SEQ ID NO:2 in 2 amino acid sites.

The results descried above show that the fusion protein provided in this invention is effective in lowering the blood glucose, when the peptide hormone is the amino acid sequence shown by SEQ ID NO:1 and the transport protein is IgG2-Fc, it could both significantly prolong the in vivo half-life of the drug and maintain the hypoglycemic efficacy of Exendin-4, as well as increase the sensitivity of the body to insulin. But when the transport protein is IgG4-Fc, the relative bioactivity of the fusion protein is lower.

The invention claimed is:

1. A fusion protein obtained by fusing a peptide hormone to a transport protein via a linker, wherein the peptide hormone is capable of lowering the blood glucose, the transport protein is the Fc fragment of the immunoglobulin IgG2, and the fusion protein is capable of lowering the blood glucose;

the peptide hormone is exendin-4, which has the amino acid sequence set forth in SEQ ID NO:1, and the linker is a peptide consisting of the sequence of $(Gly)_m$-Xaa-$(Gly)_n$, in which m is an integer between 3 and 8, n is an integer between 3 and 8, and Xaa is any one selected from the group consisting of Gly, Ser, Ala and Thr.

2. The fusion protein according to claim 1, wherein m is an integer between 4 and 6; and n is an integer between 4 and 6.

3. The fusion protein according to claim 2, wherein the linker has the amino acid sequence set forth in SEQ ID NO:3.

4. The fusion protein according to claim 1, wherein the Fc fragment of IgG2 originates from human.

5. The fusion protein according to claim 1, wherein the fusion protein has the amino acid sequence set forth in SEQ ID NO: 4.

6. A pharmaceutical composition, wherein the pharmaceutical composition comprises the fusion protein according to claim 1 and pharmacologically acceptable excipient.

7. The pharmaceutical composition according to claim 6, wherein the pharmaceutical composition is administered as local administration, aerosol or injection.

8. The pharmaceutical composition according to claim 7, wherein the injection is administered through at least one of intraperitoneal injection, subcutaneous injection, intramuscular injection or intravenous injection.

9. A method of treating diabetes or obesity, wherein the method comprises the step of administering the fusion protein according to claim 1 to subjects.

* * * * *